United States Patent [19]
Flitter et al.

[11] Patent Number: 5,658,953
[45] Date of Patent: Aug. 19, 1997

[54] PHARMACEUTICAL COMPOSITIONS OF ACETAMIDOBENZAMIDE COMPOUNDS FOR NEURODEGENERATIVE DISORDERS

[75] Inventors: William Flitter, Mountain View; William Garland, Cupertino; Richard Paylor, Sunnyvale; Allan Wilcox, Fremont, all of Calif.

[73] Assignee: Centaur Pharmaceuticals, Inc., Sunnyvale, Calif.

[21] Appl. No.: 415,694

[22] Filed: Apr. 3, 1995

[51] Int. Cl.$^6$ ................................................ A61K 31/165
[52] U.S. Cl. ............................................ 514/616; 514/619
[58] Field of Search ................................... 514/616, 619

[56] References Cited

U.S. PATENT DOCUMENTS

| | | | |
|---|---|---|---|
| 4,044,147 | 8/1977 | Nelson | 514/616 |
| 5,280,044 | 1/1994 | Crowley et al. | 514/616 |
| 5,472,983 | 12/1995 | Flitter et al. | 514/599 |

FOREIGN PATENT DOCUMENTS

| | | | |
|---|---|---|---|
| 1505633 | 3/1978 | United Kingdom | 514/599 |

OTHER PUBLICATIONS

Banasik et al., "Specific inhibitors of poly(ADP–Ribose) synthetase and mono(ADP–ribosyl)transferase" *J. Biol. Chem.* (1992) 267:1569–1575.

Beal, M.F. in *Mitochondrial Dysfunction and Oxidative Damage in Neurodegenerative Diseases*, R.G. Landes Publications Austin, TX, (1995) pp. 53–61 and 73–99.

Bishop et al., "Synthesis and in vitro evaluation of 2,3–dimethoxy–5–(fluoroalkyl)–substituted benzamides: high–affinity ligands for CNS dopamine $D_2$ receptors" *J. Med. Chem.* (1991) 34: 1612–1624.

Burns, R.S., et al., "A Primate Model of Parkinsonism . . . " *Proc. Natl. Acad. Sci USA* (1983) 80:4546–4550.

Calne, D.B., "Treatment of Parkinson's Disease" *NEJM* (Sep. 30, 1993) 329:1021–1027.

El Tayar, et al., "Interaction of neuroleptic drugs with rat striatal D–1 and D–2 dopamine receptors: a quantitative structure —affinity relationship study" *Eur. J. Med. Chem.* (1988) 23:173–182.

Gerlach, M. et al., "MPTP Mechanisms of Neurotoxicity and the Implications for Parkinson's Disease" *European Journal of Pharmacology* (1991) 208:273–286.

Heikkila, R.E., et al., "Dopaminergic Neurotoxicity of 1–Methyl–4–Phenyl–1,2,5,6–Tetrahydropyridine in Mice" *Science* (Jun. 29, 1984) 224:1451–1453.

Högberg et al., "Potential antipsychotic agents. 9. Synthesis and stereoselective dopamine D–2 receptor blockade of a potent class of substituted (R)–N–[benzyl–2–pyrrolidinyl)methyl]benzamides. Relations to other side chain congeneres" *J. Med. Chem.* (1991) 34:948–955.

Kato, T. "Reaction of Triethyloxonium Fluoroborate with Acid Amide. III$^{1)}$ Formation of Quinazoline and 4H–3, 1–Benzoxazin–4–one Derivatives". *Chem. Pharm. Bull.* (1976) 24, 3:431–436.

Katopodis et al., "Novel substrates and inhibitors of peptidylglycine $\alpha$–amidating monooxygenase" *Biochemistry* (1990) 29:4541–4548.

Langston, J.W., et al., "Chronic Parkinsonism in Humans Due to a Product of Meperidine–Analog Synthesis" *Science* (Feb. 25, 1983) 219, 979–980.

Marsden, C.D., in "Review Article —Parkinson's Disease" *Lancet* (Apr. 21, 1990) 948–952.

Mizuno, Y., Mori, H., Kondo, T. "Potential of Neuroprotective Therapy in Parkinson's Disease" *CNS Drugs* (1994) 1:45–46.

Monković et al., "Potential non–dopaminergic gstrointestinal prokinetic agents in the series of substituted benzamides" *Eur. J. Med. Chem.* (1989) 24:233–240.

Rainnie et al., "Adenosine inhibition of mesopontine cholinergic neurons: implications for EEG arousal" *Science* (1994) 263:689–690.

Singer, T.P., et al., "Biochemical Events in the Development of Parkinsonism . . . " *J. Neurochem.* (1987) 1–8.

Chemical Abstract, vol. 99, #53310c (1983).

*Primary Examiner*—James H. Reamer
*Attorney, Agent, or Firm*—Burns, Doane, Swecker & Mathis, L.L.P.

[57] ABSTRACT

A group of benzamide compounds are disclosed which are useful for treating neurodegenerative disorders. Methods for making these compounds are provided. These materials are formed into pharmaceutical compositions for oral or intravenous administration to patients suffering from conditions such as Parkinson's disease which can exhibit themselves as progressive loss of central nervous system function. The compounds can arrest or slow the progressive loss of function.

26 Claims, No Drawings

PHARMACEUTICAL COMPOSITIONS OF ACETAMIDOBENZAMIDE COMPOUNDS FOR NEURODEGENERATIVE DISORDERS

FIELD OF THE INVENTION

This invention concerns benzamide compounds, pharmaceutical compositions containing these compounds, and their use to treat or protect against neurodegenerative conditions.

BACKGROUND INFORMATION

Neurodegenerative disease encompasses a range of seriously debilitating conditions including Parkinson's disease, amyotrophic lateral sclerosis (ALS, "Lou Gehrig's disease"), multiple sclerosis, Huntington's disease, Alzheimer's disease, diabetic retinopathy, multi-infarct dementia, macular degeneration and the like. These conditions are characterized by a gradual but relentless worsening of the patient's condition over time. The mechanisms and causes of these diseases are becoming better understood and a variety of treatments have been suggested. One of these neurodegenerative conditions, Parkinson's disease, is associated with abnormal dopamine depletion in selected regions of the brain.

Recent summaries of the state of understanding of Parkinson's disease are provided by Marsden, C. D., in "Review Article—Parkinson's Disease" *Lancet* (Apr. 21, 1990) 948–952 and Calne, D. B., in "Treatment of Parkinson's Disease" *NEJM* (Sept. 30, 1993) 329:1021–1027. As these reviews point out, dopamine deficiency was identified as a key characteristic of Parkinson's disease, and the destruction of the dopaminergic nigrostriatal pathway paralleled dopamine depletion in Parkinson's patients.

Rapid development of Parkinson's-like symptoms in a small population of illicit drug users in the San Jose, Calif. area was linked to trace amounts of a toxic impurity in the home-synthesized drugs. Subsequent studies in animal models, including monkeys, demonstrated that 1-methyl-4-phenyl-1,2,5,6-tetrahydropyridine (MPTP) was the cause of the Parkinson's-like symptoms which developed in the illicit drug users, as reported by J. W. Langston et al., in "Chronic Parkinsonism in Humans Due to a Product of Meperidine-Analog Synthesis" *Science* (Feb. 25, 1983) 219, 979–980. These early findings and the many studies that they stimulated led to the development of reliable models for Parkinson's disease, as reported by Heikkila, R. E., et al., in "Dopaminergic Neurotoxicity of 1-Methyl-4-Phenyl-1,2,5, 6-Tetrahydropyridine in Mice" *Science* (Jun. 29, 1984) 224:1451–1453; Burns, R. S., et al., in "A Primate Model of Parkinsonism . . . " *Proc. Natl. Acad. Sci USA* (1983) 80:4546–4550; Singer, T. P., et al., "Biochemical Events in the Development of Parkinsonism . . . " *J. Neurochem.* (1987) 1–8; and Gerlach, M. et al., "MPTP Mechanisms of Neurotoxicity and the Implications for Parkinson's Disease" *European Journal of Pharmacology* (1991) 208:273–286. These references and others describe studies to help explain the mechanism of how the administration of MPTP to animals gives rise to motor defects characteristic of Parkinson's disease. They clearly indicate that MPTP was the cause of the Parkinson's-like symptoms that developed in the humans who had used the tainted illicit drugs and that similar motor deficits were found in other primates and other test animals which had been dosed directly with MPTP. They further point out that the administration of MPTP induces a marked reduction in the concentration of dopamine in the test subjects.

These findings have led to the development of an assay for agents effective in treating dopamine-associated neurodegenerative disorders, such as Parkinson's disease. In this assay, test animals are given an amount of MPTP adequate to severely depress their dopamine levels. Test compounds are administered to determine if they are capable of preventing the loss of dopamine in the test animals. To the extent that dopamine levels are retained, a compound can be considered to be an effective agent for slowing or delaying the course of neurodegenerative disease, e.g., Parkinson's disease.

Mitochondrial function is associated with many neurodegenerative diseases such as ALS, Huntington's disease, Alzheimer's disease, cerebellar degeneration, and aging itself (Beal, M. F. in *Mitochondrial Dysfunction and Oxidative Damage in Neurodegenerative Diseases*, R. G. Landes Publications Austin, Tex., 1995 at, for example, pages 53–61 and 73–99). Mitochondrial damage is the mechanism by which MPTP depletes dopamine concentrations in the striatum (Mizuno, Y., Mori, H., Kondo, T. in "Potential of Neuroprotective Therapy in Parkinson's Disease" *CNS Drugs* (1994) 1:45–46). Thus, an agent which protects from mitochondrial dysfunction caused by MPTP could be useful in treating diseases of the central nervous system in which the underlying cause is mitochondrial dysfunction.

While other benzamide compounds are known, their utility heretofore has generally been as intermediates in chemical syntheses or in fields unrelated to the present invention. Slight structural changes yielded large differences in efficacy and toxicity. The vast majority of benzamide compounds have little or no activity in our screens. However, there are reports of biological activity for other, strutrurally different benzamides. These reports include:

El Tayar et al., "Interaction of neuroleptic drugs with rat striatal D-1 and D-2 dopamine receptors: a quantitative structure—affinity relationship study" *Eur. J. Med. Chem.* (1988) 23:173–182;

Monkovic̀ et al., "Potential non-dopaminergic gastrointestinal prokinetic agents in the series of substituted benzamides" *Eur. J. Med. Chem.* (1989) 24:233–240;

Banasik et al., "Specific inhibitors of poly(ADP-Ribose) synthetase and mono(ADP-ribosyl)transferase" *J. Biol. Chem.* (1992) 267:1569–1575;

Bishop et al., "Synthesis and in vitro evaluation of 2,3-dimethoxy-5-(fluoroalkyl)-substituted benzamides: high-affinity ligands for CNS dopamine $D_2$ receptors" *J. Med. Chem.* (1991) 34:1612–1624;

Högberg et al., "Potential antipsychotic agents. 9. Synthesis and stereoselective dopamine D-2 receptor blockade of a potent class of substituted (R)-N-[benzyl-2-pyrrolidinyl)methyl]benzamides. Relations to other side chain congeners" *J. Med. Chem.* (1991) 34:948–955;

Katopodis et al., "Novel substrates and inhibitors of peptidylglycine α-amidating monooxygenase" *Biochemistry* (1990) 29:4541–4548; and Rainnie et al., "Adenosine inhibition of mesopontine cholinergic neurons: implications for EEG arousal" *Science* (1994) 263:689–690.

Other benzamide-containing pharmaceutical compositions and their use to treat or protect against neurodegenerative conditions were disclosed in commonly owned U.S. patent application Ser. No. 08/227,777 filed Apr. 14, 1994, (now U.S. Pat. No. 5,472,983) the disclosure of which is incorporated herein by reference in its entirety.

STATEMENT OF THE INVENTION

It has now been found that a family of novel acetamidobenzamide compounds of the Formula I below exhibit strong activity against Parkinson's disease as measured by their ability to prevent MPTP-induced reduction of dopamine levels.

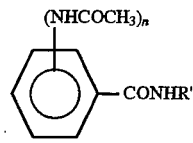

where R' is a straight, branched or cyclic saturated alkyl of from 3 to 5 carbon atoms and n is 1 or 2.

It has also been found that the novel nitro- and aminobenzamide compounds N-tert-amyl-4-nitrobenzamide (CPI1033), N-1,2-dimethylpropyl-4-nitrobenzamide (CPI1085), N-n-butyl-3-nitrobenzamide (CPI1135), N-n-pentyl-4-nitrobenzamide (CPI1140), N-2-methylbutyl-4-nitrobenzamide (CPI1146), N-n-butyl-3,5-dinitrobenzamide (CPI1147), N-methylcyclopropyl-4-nitrobenzamide (CPI1164), N-n-butyl-2-nitrobenzamide (CPI1173), N-n-pentyl-2-nitrobenzamide (CPI1174), and N-methylcyclopropyl-4-aminobenzamide (CPI1240) are useful as intermediates for preparing the acetamide compounds of Formula I above and as pharmaceutical agents.

These nitro- and aminobenzamide compounds and the acetamidobenzamide compounds of Formula I constitute one aspect of the invention.

The invention can also take the form of pharmaceutical compositions based on one or more of the compounds of Formula II below:

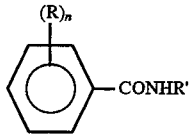

where R' is a saturated alkyl of from 3 to 5 carbon atoms, each R is independently —NH—CO—CH$_3$, —NO$_2$ or —NH$_2$, and n is 1 or 2, with the following provisos: 1) when n is 1 and R is —NO$_2$ at the 4 position of the ring, R' is not tert-butyl, iso-butyl, or propyl; 2) when n is 1 and R is —NO$_2$ at the 2 position of the ring, R' is not iso-butyl or propyl; and 3) when n is 2 and R' is tert-butyl and both Rs are —NO$_2$, the R groups are not at the 3 and 5 positions of the ring.

The invention can further take the form of methods of treating neurodegenerative conditions using these materials.

Thus, in one aspect this invention provides the novel acetamidobenzamide compounds of the Formula I and the novel nitro- and aminobenzamides described above.

In another aspect this invention provides pharmaceutical compositions which include one or more benzamide compounds of the Formula II in a pharmaceutically acceptable carrier. This carrier is preferably an oral carrier but can be an injectable carrier as well. These pharmaceutical compositions can be in bulk form but more typically are presented in unit dosage form.

In another aspect this invention provides a method for treating a patient suffering from a dopamine-associated neurodegenerative condition. This method involves administering to the patient an effective neurodegenerative condition-treating mount of one or more of the pharmaceutical compositions just described.

In another aspect this invention provides a method for treating a patient suffering from a condition characterized by progressive loss of central nervous system function. This method involves administering to the patient with loss of central nervous system function an effective mount of one or more of the pharmaceutical compositions just described.

In a most important aspect this invention provides a method for treating a patient suffering from a progressive loss of central nervous system function associated with Parkinson's disease. This method involves administering (preferably orally) to the patient with loss of progressive central nervous system function an effective amount of one or more of the pharmaceutical compositions just described.

In another aspect this invention provides a method for treating a patient suffering from a condition characterized by progressive loss of nervous system function due to mitochondrial dysfunction. This method involves administering to the patient with loss of central nervous system function an effective amount of one or more of the pharmaceutical compositions just described.

In a further aspect, this invention provides methods for preparing the compounds of Formula I and II. These methods generally involve condensing an alkyl amine of from 3 to 5 carbon atoms with a mono or dinitro benzoyl halide having the nitro configuration corresponding to the nitro, amine or acetamide substitution desired in the final compound, optionally, reducing the nitro groups, and, optionally, converting the amino benzamides to acetoamidobenzamides by reaction with an acetylhalide.

DETAILED DESCRIPTION OF THE INVENTION

The Compounds

This invention provides novel acetamidobenzamide compounds of the Formula I below and their use as active pharmaceutical agents.

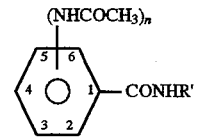

where R' is a saturated alkyl of from 3 to 5 carbon atoms and n is 1 or 2.

The acetamido group may be found anywhere on the ring. Preferred embodiments include when n is 1 and the R group is at the 2, 3 or 4 position of the ring and when n is 2 and the R groups are at the 2 and 3, 2 and 4, 2 and 5, 2 and 6, 3 and 4, or 3 and 5 positions of the ring.

With respect to the alkyl substituents, compounds wherein R' is an alkyl which does not have a hydrogen on the alpha carbon, that is, the carbon which bonds to the nitrogen of the ring, are preferred. Examples of these preferred R' groups are tert-butyl and tert-amyl.

The benzamide of the Formula I above which is N-tert-butyl-4-acetamidobenzamide is referred to elsewhere in this specification by the internal compound designation number CPI1189.

The benzamide of the Formula I above which is N-iso-propyl-4-acetamidobenzamide is referred to elsewhere in this specification by the internal compound designation number CPI1232.

The benzamide of the Formula I above which is N-tert-amyl-4-acetamidobenzamide is referred to elsewhere in this specification by the internal compound designation number CPI1233.

The benzamide of the Formula I above which is N-tert-butyl-3-acetamidobenzamide is referred to elsewhere in this specification by the internal compound designation number CPI1234.

The benzamide of the Formula I above which is N-methylcyclopropyl-4-acetamidobenzamide is referred to elsewhere in this specification by the internal compound designation number CPI1241.

The compounds N-tert-butyl 4-acetamidobenzamide (CPI1189), N-iso-propyl-4-acetamidobenzamide (CPI1232), N-tert-amyl-4-acetamidobenzamide CPI1233), N-tert-butyl-3-acetamidobenzamide (CPI1234), and N-methylcyclopropyl-4-acetamidobenzamide (CPI1241)are the most preferred compounds of the Formula I at this time.

The invention also provides the following novel nitro- and aminobenzamide compounds which are useful both as intermediates in preparing the compounds of the Formula I and as active pharmaceutical agents: N-tert-amyl-4-nitrobenzamide (CPI1033), N-1,2-dimethylpropyl-4-nitrobenzamide (CPI1085), N-n-butyl-3-nitrobenzamide (CPI1135), N-n-pentyl-4-nitrobenzamide (CPI1140), N-2-methylbutyl-4-nitrobenzamide (CPI1146), N-n-butyl-3,5-dinitrobenzamide (CPI1147), N-methylcyclopropyl-4-nitrobenzamide (CPI1164), N-n-butyl-2-nitrobenzamide (CPI1173), N-n-pentyl-2-nitrobenzamide (CPI1174), and N-methylcyclopropyl-4-aminobenzamide (CPI1240).

The benzamide which is N-tert-amyl-4-nitrobenzamide is referred to elsewhere in this specification by the internal compound designation number CPI1033.

The benzamide which is N-1,2-dimethylpropyl-4-nitrobenzamide is referred to elsewhere in this specification by the internal compound designation number CPI1085.

The benzamide which is N-n-butyl-3-nitrobenzamide is referred to elsewhere in this specification by the internal compound designation number CPI1135.

The benzamide which is N-n-pentyl-4-nitrobenzamide is referred to elsewhere in this specification by the internal compound designation number CPI1140.

The benzamide which is N-2-methylbutyl-4-nitrobenzamide is referred to elsewhere in this specification by the internal compound designation number CPI1146.

The benzamide which is N-n-butyl-3,5-dinitrobenzamide is referred to elsewhere in this specification by the internal compound designation number CPI1147.

The benzamide which is N-methylcyclopropyl-4-nitrobenzamide is referred to elsewhere in this specification by the internal compound designation number CPI1164.

The benzamide which is N-n-butyl-2-nitrobenzamide is referred to elsewhere in this specification by the internal compound designation number CPI1173.

The benzamide which is N-n-pentyl-2-nitrobenzamide is referred to elsewhere in this specification by the internal compound designation number CPI1174.

The benzamide which is N-methylcyclopropyl-4-aminobenzamide is referred to elsewhere in this specification by the internal compound designation number CPI1240.

When the benzamide compound contains an amino group, such as CPI 1240, this functionality can be present as such or as a pharmaceutically acceptable salt. When these "compounds" are referred to it is to be understood that these salts are included as well.

Commonly owned U.S. patent application Ser. No. 08/227,777, referred to above, discloses several benzamides useful in treating neurodegenerative diseases based on their protective action in the MPTP mouse model of Parkinson's disease. The compound N-tert-butyl 4-acetamidobenzamide (CPI1189) of the present invention is an in vivo biotransformation product of one of these benzamides (N-tert-butyl 4-nitrobenzamide (CPI1020)) which is found in the blood of rats and mice to which CPI1020 has been administered orally. This compound is likely formed in the body by reduction of the ring nitro of CPI1020 to an amino moiety (CPI1160) followed by acetylation of the amino function.

The compounds of the present invention, as exemplified by CPI1189, are much more potent than CPI1020 (approximately 10 times as potent) in protecting mice from dopamine reduction in the striatum induced by s.c. treatment with MPTP. Based on structurally similar molecules such as acetaminophen which contain an acetamido functionality, they should also be safer than CPI1020 because they would not be metabolized in the body to result in metabolites containing hydroxylamines (likely to be Ames positive) nor would they be likely to result in amino metabolites which may have cardiovascular and/or anorexic effects.

Pharmaceutical Compositions

The benzamide compounds of the Formula II below:

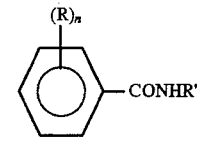

where R' is a straight or branched chain saturated alkyl of from 3 to 5 carbon atoms, each R is independently —NH—CO—CH$_3$, —NO$_2$ or —NH$_2$, and n is 1 or 2, with the following provisos: 1) when n is 1 and R is —NO$_2$ at the 4 position of the ring, R' is not tert-butyl, iso-butyl, or propyl; 2) when n is 1 and R is —NO$_2$ at the 2 position of the ring, R' is not iso-butyl or propyl; and 3) when n is 2 and R' is tert-butyl and both Rs are —NO$_2$, the R groups are not at the 3 and 5 positions of the ring, are formulated into pharmaceutical compositions suitable for oral or other appropriate routes of administration.

The benzamide of the Formula II above which is N-iso-propyl-4-nitrobenzamide is referred to elsewhere in this specification by the internal compound designation number CPI1026.

The benzamide of the Formula II above which is N-tert-butyl-3-nitrobenzamide is referred to elsewhere in this specification by the internal compound designation number CPI1034.

The benzamide of the Formula II above which is N-tert-butyl-2-nitrobenzamide is referred to elsewhere in this specification by the internal compound designation number CPI1035.

The benzamide of the Formula II above which is N-n-butyl-4-nitrobenzamide is referred to elsewhere in this specification by the internal compound designation number CPI1045.

The benzamide of the Formula II above which is N-n-propyl-4-nitrobenzamide is referred to elsewhere in this specification by the internal compound designation number CPI1047.

The benzamide of the Formula II above which is N-tert-butyl-3,5-dinitrobenzamide is referred to elsewhere in this specification by the internal compound designation number CPI1049.

The benzamide of the Formula II above which is N-1-methylpropyl-4-nitrobenzamide is referred to elsewhere in this specification by the internal compound designation number CPI1084.

The benzamide of the Formula II above which is N-tert-butyl-4-aminobenzamide is referred to elsewhere in this specification by the internal compound designation number CPI1160.

The benzamide of the Formula II above which is N-tert-butyl-3-aminobenzamide is referred to elsewhere in this specification by the internal compound designation number CPI1248.

When R is —NH$_2$, the compounds of the Formula II may be used as salts in which the amine group is protonated to the cation form, in combination with a pharmaceutically acceptable artion, such as chloride, bromide, iodide, hydroxyl, nitrate, sulfonate, methane sulfonate, acetate, tartrate, oxalate, suecinate, or palmoate.

Pharmaceutical compositions using the compounds N-tert-butyl 4-acetamidobenzamide (CPI1189), N-tert-butyl-3-acetamidobenzamide (CPI1234), N-tert-amyl-4-acetamidobenzamide (CPI1233), N-tert-butyl-4-aminobenzamide (CPI1160), N-tert-butyl-3-nitrobenzamide (CPI1034), and N-tert-butyl-3-aminobenzamide (CPI1248) are most preferred at this time.

The compositions for oral administration can take the form of bulk liquid solutions or suspensions, or bulk powders. More commonly, however, the compositions are presented in a unit dosage form to facilitate accurate dosing. Typical unit dosage forms include prefilled, premeasured ampules or syringes of the liquid compositions or pills, tablets, capsules or the like in the case of solid compositions. In such compositions, the benzamide compound is usually a minor component (0.1 to say 50% by weight or preferably from about 1 to about 40% by weight) with the remainder being various vehicles or carriers and processing aids helpful for forming the desired dosing form. A liquid form may include a suitable aqueous or nonaqueous vehicle with buffers, suspending and dispensing agents, colorants, flavors and the like.

A solid form may include, for example, any of the following ingredients, or compounds of a similar nature: a binder such as microcrystalline cellulose, gum tragacanth or gelatin; an excipient such as starch or lactose, a disintegrating agent such as alginie acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

In the case of injectable compositions, they are commonly based upon injectable sterile saline or phosphate-buffered saline or other injectable carriers known in the art. Again the active benzamide is typically a minor component, often being from about 0.05 to 10% by weight with the remainder being the injectable carrier and the like.

These components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Penn., which is incorporated by reference.

One can also administer the compounds of the invention in sustained release forms or from sustained release drug delivery systems. A description of representative sustained release materials can be found in the incorporated materials in *Remington's Pharmaceutical Sciences*.

Conditions Treated and Treatment Regimens

The conditions treated with the benzamide-containing pharmaceutical compositions may be classed generally as neurodegenerative conditions. These include conditions characterized by protracted low grade stress upon the central nervous system and gradual progressive loss of central nervous system function. These conditions include Parkinson's disease, amyotrophic lateral sclerosis (ALS, "Lou Gehrig's disease"), multiple sclerosis, Huntington's disease, Alzheimer's disease, diabetic retinopathy, multi-infarct dementia, macular degeneration and the like. Each of these conditions is characterized by a progressive loss of function. The benzamide compound-containing pharmaceutical compositions of this invention, when administered orally or by injection such as intravenously, can slow and delay and possibly even to some extent reverse the loss of function.

Injection dose levels for treating these conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

With these neurodegenerative conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 1 to about 20 mg/kg of benzamide, with preferred doses each providing from about 1 to about 10 mg/kg and especially about 1 to about 5 mg/kg.

Of course, one can administer the benzamide compound as the sole active agent or one can administer it in combination with other agents, including other active benzamide compounds.

Methods of Preparation of Compounds

The benzamide compounds of this invention can be prepared using commonly available starting materials and readily achievable reactions.

One representative preparation route, which is illustrated with tert-butyl amine, but which may be used with any alkyl amine, involves the following reactions:

(A)

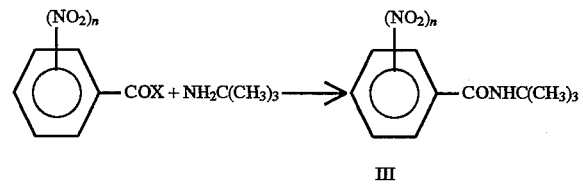

where X is halo such as I, Br, F or Cl.

(B)

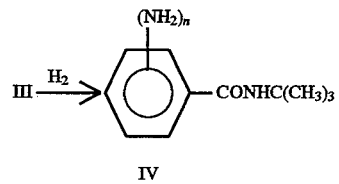

(C)

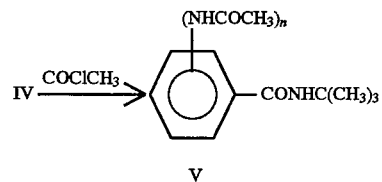

In step (A) the N-tert-butyl nitrobenzamides (III) are formed. This reaction must be carried out at temperatures below 10° C.

This step (A) yields as benzamides III, the compounds of the invention where R is —NO$_2$.

In step (B) the vitro groups in the mono- or di-nitro benzamide III are subjected to reduction. This is commonly carried out with a reducing agent such as hydrazine and an appropriate catalyst such as a heterogeneous platinum, iron oxide hydroxide, palladium or nickel catalyst, typically on a support, or with hydrogen gas and a catalyst.

This step (B) yields as benzamides IV, the compounds of the invention where R is $NH_2$.

In step (C) the amino-benzamides IV are converted to acetamidobenzamides V by reaction with an acetyl halide such as acetylchloride. This reaction is carried out in the presence of a mild base and at low to ambient temperatures such as −20° C. to +20° C. This yields the compounds of the invention where R is acetamido.

Alternate synthetic schemes may also be used to prepare the compounds of the present invention. Examples of these alternate routes are set forth below using CPI1189 as the representative compound. Other compounds may be prepared using these alternate methods by starting with appropriate starting materials, such as 2- or 3-amino- or nitro-benzonitrile or 2,3-, 2,4-, 2,5-, 2,6-, 3,4- or 3,5-diamino- or dinitro-benzonitrile and the appropriate alcohol (Alternate Route 1) or similarly substituted toluene compounds and the appropriate alkyl amine (Alternate Route 3).

Alternate Route 1

This route begins with acetylation of, for example, 4-aminobenzonitrile (A) to compound (B) using standard methods. Acid hydrolysis of tert-butanol in the presence of 4-acetamidobenzonitrile (B), provides a feasible synthetic pathway to CPI1189.

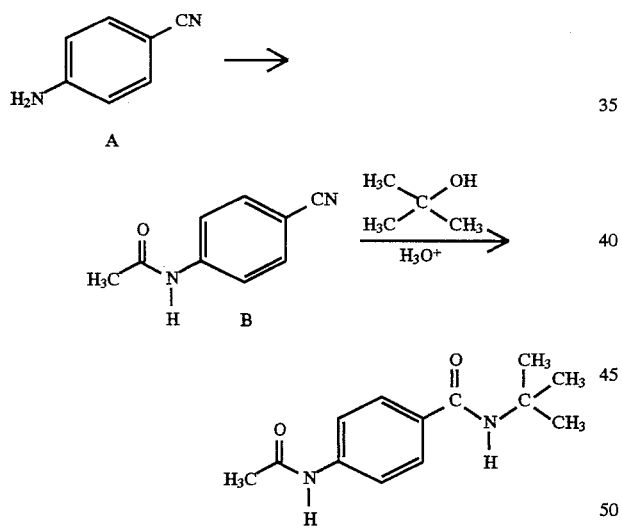

Alternate Route 2

Acetylation, using standard methods, of the inexpensive starting material PABA (C) affords a cheap method to produce 4-acetamidobeazoic acid (D). Conversion of (D) to the acid chloride (E) using standard methods (e.g., $SOCl_2$) and subsequent amidation using standard methods, such as those described previously, produces CPI1189 from inexpensive raw materials.

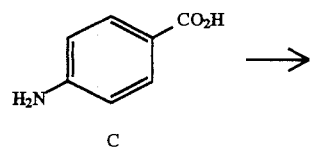

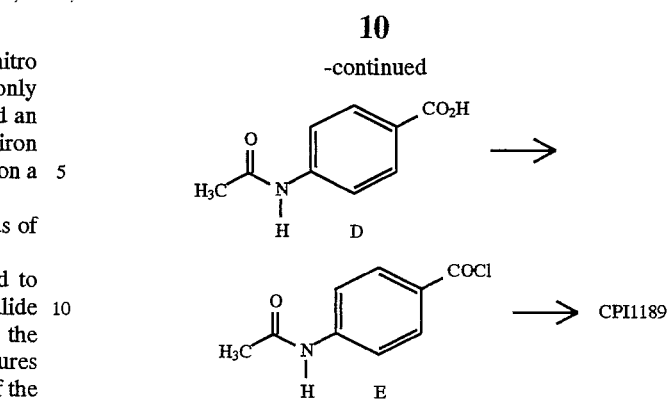

Alternate Route 3

Another method for the preparation of the compounds of the present invention begins with acetylation, using standard methods, of, for example, paratoluidine (F) to 4-acetamidotoluene (G). The synthetic intermediate (G) may be converted to 4-acetamidobenzoic acid (D) with common oxidizing agents (e.g., $KMnO_4$) and subsequently transformed to CPI1189 as outlined in Alternate Route 2.

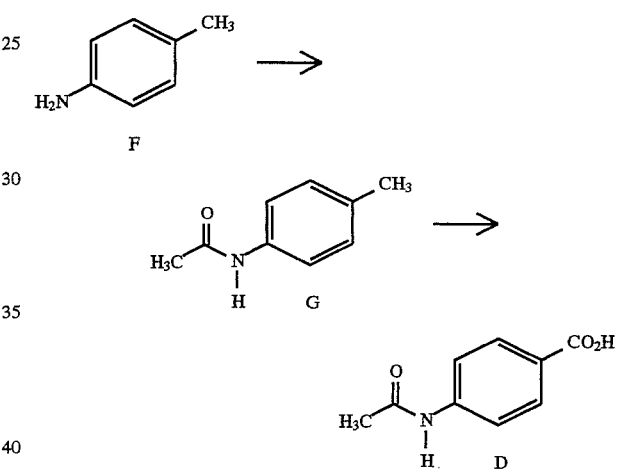

EXAMPLES

The invention will be further described by the following Examples. These are provided to illustrate several preferred embodiments of the invention but are not to be construed as limiting its scope which is, instead, defined by the appended claims. Examples 1 to 19 demonstrate the preparation of acetamidobenzamides, as well as nitro- and aminobenzamides, which are representative of the benzamide compounds employed in the compositions and methods of this invention. Examples 20 to 24 demonstrate the pharmaceutical pharmaceutical compositions based on the compounds. Th test results illustrating the activity of the compositions of the invention are provided.

Example 1

Preparation of N-tert-butyl-4-aminobenzamide (CPI1160)

tert-Butyl amine (14.6 g, 0.200 mole) was stirred in ethyl acetate (150 mL, purified by washing with 5% sodium carbonate solution, saturated sodium chloride solution, drying over anhydrous magnesium sulfate, and filtering through fluted filter paper) and cooled to 5° C. with an ice bath. 4-nitrobenzoyl chloride (18.6 g, 0.100 mole) in purified ethyl acetate (75 mL) was added dropwise at such a rate to maintain the temperature below 10° C. The ice bath was removed upon complete addition of benzoyl chloride solution and the reaction stirred for 4 hours. The reaction mixture was then filtered on a Büchner funnel, the filtrate washed three times with 5% HCl , once with saturated sodium chloride, dried over anhydrous magnesium sulfate, filtered through fluted filter paper, and the solvent stripped off leaving white crystalline product. The product was dried in a vacuum oven at 24 mm and 45° C. for 14 hours. This procedure produced 17.13 g of crystals of N-tert-butyl-4-nitrobenzamide (CPI1020) (77% yield), mp 162°–163° C. Proton nuclear magnetic resonance (89.55 MHz in $CDCl_3$) showed absorptions at 8.257 ppm (d, 8.8 Hz, 2H; 3,5-aryl H); 7.878 ppm (d, 8.8 Hz, 2H; 2,6-aryl H); 6.097 ppm (bs, 1H; N—H); 1.500 ppm (s, 9H; tert-butyl H).

Palladium on carbon (5%, 75 mg) was added to CPI-1020 (5 g, 22.5 mmole) in 95% ethanol at 55° C. A solution of hydrazine (1.2 mL) in 95% ethanol (10 mL) was added dropwise over 30 min. and more Pd/C added (75 mg). The reaction was refluxed 3 hours, hydrazine (0.5 g) in 95% ethanol (5 mL) was added and the reaction was refluxed for another hour. The reaction was filtered on a buchner funnel, the volume of solvent reduced under vacuum, and extracted with dichloromethane. The combined extracts were dried over magnesium sulfate and solvent stripped, leaving 3.90 g of N-tert-butyl-4-aminobenzamide (CPI1160) (90% yield), melting point 125°–127° C. 90 MHz proton NMR (in $CDCl_3$) showed absorbances at 7.290 ppm (2H, d, 8.8 Hz; 2,6 aryl H); 6.368 ppm (2H, d, 8.8 Hz; 3,5 aryl H); 5.45 ppm (1 H, bs; NHC=O); 3.727 ppm (2H, bs, aryl-$NH_2$); 1.186 ppm (9H, s; t-butyl H).

Example 2

Preparation of N-tert-butyl-4-acetamidobenzamide (CPI1189)

Acetyl chloride (0.45 g, 5.7 mmole) in ethyl acetate (25 mL) was added dropwise to CPI-1160 (1.0 g, 5.2 mmole) and triethyl amine (0.58 g, 5.7 mmole) in ethyl acetate at 3° C. at such a rate to maintain the temperature below 10° C. The reaction was allowed to warm to room temperature, stirred 1 hour, and washed with 5% HCl. Recrystallization from acetone gave 1.08 g N-tert-butyl-4-acetamidobenzamide (CPI1189)(89% yield), melting point 119°–121° C. 90 MHz proton NMR (in DMSO-d6) showed absorbances at 9.726 ppm (1H, bs, N—H); 7.715 ppm (4H, dd, 4.4 Hz; aryl H); 7.295 ppm (1 H, bs; NH); 2.844 ppm (3H, s; $CH_3CO$); 1.448 ppm (9H, s; t-butyl H).

Example 3

Preparation of N-tert-butyl-3-acetamidobenzamide (CPI1234)

The amidation procedures of Example 1 were followed using 3-nitrobenzoyl chloride instead of 4-nitrobenzoyl chloride. This gave N-tert-butyl-3-nitrobenzamide (CPI1034) in 92% yield, melting point 123°–125° C. Proton NMR (in $CDCl_3$) showed absorptions at 8.517 ppm (2-aryl H, s, 1H); 8.337 ppm (4-aryl H, d, 8.8 Hz, 1H); 8.121 ppm (6-aryl H, d, 6.4 Hz, 1H); 7.618 ppm (5-aryl H, m, 1H); 6.032 ppm (N—H, bs, 1H); 1.484 ppm (t-butyl H, s, 9H).

Iron (III) oxide hydroxide catalyzed hydrazine reduction produced N-tert-butyl-3-aminobenzamide (CPI1248) in 53% yield, melting point 118°–120° C. Proton NMR (in $CDCl_3$) showed absorbances at 7.088 ppm (4–6-aryl H, m, 3H); 6.794 ppm (2-aryl H, s, 1H); 5.902 ppm (N—H, bs, 1H); 3.145 ppm (aryl N—H, bs, 2H); 1.458 ppm (t-butyl H, s, 9H).

Acetylation of CPI1248 as described in Example 2 gave N-tert-butyl-3-acetamidobenzamide (CPI1234) in 75% yield, melting point 194°–195° C. Proton NMR (in $CDCl_3$) showed absorptions at 7.778 ppm (4–6-aryl H, m, 3H); 7.392 ppm (2-aryl H, s, 1H); 6.08 ppm (N—H, bs, 1H); 2.174 ppm (acetyl $CH_3$, s, 9H); 1.500 ppm (t-butyl H, s, 9H).

Example 4

Preparation of N-tert-butyl-2-acetamidobenzamide

The method of Example 3 is repeated using 2-nitrobenzoyl chloride in the amidation step. This yields N-tert-butyl-2-nitrobenzamide (CPI1035).

Reduction of the nitrobenzamide with hydrazine yields N-tert-butyl-2-aminobenzamide.

Acetylation of the aminobenzamide yields N-tert-butyl-2-acetamidobenzmnide.

Example 5

Preparation of N-iso-propyl-4-acetamidobenzamide (CPI1232)

The method of Example 3 is repeated using 4-nitrobenzoyl chloride and iso-propyl amine in the amidation step. This yields N-iso-propyl-4-nitrobenzamide (CPI1026).

Reduction of the nitrobenzamide with hydrazine yields N-iso-propyl-4-aminobenzamide.

Acetylation of the aminobenzamide yields N-iso-propyl-4-acetamidobenzamide (CPI1232).

Example 6

Preparation of N-tert-amyl-4-acetamidobenzamide (CPI1233)

The method of Example 3 is repeated using 4-nitrobenzoyl chloride and tert-amyl amine in the amidation step. This yields N-tert-amyl-4-nitrobenzamide (CPI1033).

Reduction of the nitrobenzamide with hydrazine yields N-tert-amyl-4-aminobenzamide.

Acetylation of the aminobenzamide yields N-tert-amyl-4-acetamidobenzamide (CPI1233).

Example 7

Preparation of N-iso-butyl-4-acetamidobenzamide

The method of Example 3 is repeated using 4-nitrobenzoyl chloride and iso-butyl amine in the amidation step. This yields N-iso-butyl-4-nitrobenzamide (CPI1044).

Reduction of the nitrobenzamide with hydrazine yields N-iso-butyl-4-aminobenzamide.

Acetylation of the aminobenzamide yields N-iso-butyl-4-acetamidobenzamide.

Example 8

Preparation of N-n-butyl-4-acetamidobenzamide

The method of Example 3 is repeated using 4-nitrobenzoyl chloride and n-butyl amine in the amidation step. This yields N-n-butyl-4-nitrobenzamide (CPI1045).

Reduction of the nitrobenzamide with hydrazine yields N-n-butyl-4-aminobenzamide.

Acetylation of the aminobenzamide yields N-n-butyl-4-acetamidobenzamide.

Example 9

Preparation of N-n-propyl-4-acetamidobenzamide

The method of Example 3 is repeated using 4-nitrobenzoyl chloride and n-propyl amine in the amidation step. This yields N-n-propyl-4-nitrobenzamide (CPI1047).

Reduction of the nitrobenzamide with hydrazine yields N-n-propyl-4-aminobenzamide.

Acetylation of the aminobenzamide yields N-n-propyl-4-acetamidobenzamide.

Example 10

Preparation of N-1,2-(dimethylpropyl-4-acetamidobenzamide

The method of Example 3 is repeated using 4-nitrobenzoyl chloride and 1,2-dimethylpropyl amine in the amidation step. This yields N-1,2-dimethylpropyl-4-nitrobenzamide (CPI1085).

Reduction of the nitrobenzamide with hydrazine yields N-1,2-dimethylpropyl-4-aminobenzamide.

Acetylation of the aminobenzamide yields N-1,2-dimethylpropyl-4-acetamidobenzamide.

Example 11

Preparation of N-n-pentyl-4-acetamidobenzamide

The method of Example 3 is repeated using 4-nitrobenzoyl chloride and n-pentyl amine in the amidation step. This yields N-n-pentyl-4-nitrobenzamide (CPI1140).

Reduction of the nitrobenzamide with hydrazine yields N-n-pentyl-4-aminobenzamide.

Acetylation of the aminobenzamide yields N-n-pentyl-4-acetamidobenzamide.

Example 12

Preparation of N-2-methylbutyl-4-acetamidobenzamide

The method of Example 3 is repeated using 4-nitrobenzoyl chloride and 2-methylbutyl amine in the amidation step. This yields N-2-methylbutyl-4-nitrobenzamide (CPI1146).

Reduction of the nitrobenzamide with hydrazine yields N-2-methylbutyl-4-aminobenzamide.

Acetylation of the aminobenzamide yields N-2-methylbutyl-4-acetamidobenzamide.

Example 13

Preparation of N-n-pentyl-2-acetamidobenzamide

The method of Example 3 is repeated using 2-nitrobenzoyl chloride and n-pentyl amine in the amidation step. This yields N-n-pentyl-2-nitrobenzamide (CPI1174).

Reduction of the nitrobenzamide with hydrazine yields N-n-pentyl-2-aminobenzamide.

Acetylation of the aminobenzamide yields N-n-pentyl-2-acetamidobenzamide.

Example 14

Preparation of N-tert-butyl-2,3-diacetamidobenzamide

The method of Example 3 is repeated using 2,3-dinitrobenzoyl chloride in the amidation step. This yields N-tert-butyl-2,3-dinitrobenzamide.

Reduction of the nitrobenzamide with hydrazine yields N-tert-butyl-2,3-diaminobenzamide.

Acetylation of the aminobenzamide yields N-tert-butyl-2,3-diacetamidobenzamide.

Example 15

Preparation of N-tert-amyl-2,4-diacetamidobenzamide

The method of Example 3 is repeated using 2,4-dinitrobenzoyl chloride and tert-amyl amine in the amidation step. This yields N-tert-amyl-2,4-dinitrobenzamide.

Reduction of the nitrobenzamide with hydrazine yields N-tert-amyl-2,4-diaminobenzamide.

Acetylation of the aminobenzamide yields N-tert-amyl-2,4-diacetamidobenzamide.

Example 16

Preparation of N-tert-butyl-2,5-diacetamidobenzamide

The method of Example 3 is repeated using 2,5-dinitrobenzoyl chloride in the amidation step. This yields N-tert-butyl-2,5-dinitrobenzamide.

Reduction of the nitrobenzamide with hydrazine yields N-tert-butyl-2,5-diaminobenzamide.

Acetylation of the aminobenzamide yields N-tert-butyl-2,5-diacetamidobenzamide.

Example 17

Preparation of N-tert-butyl-2,6-diacetamidobenzamide

The method of Example 3 is repeated using 2,6-dinitrobenzoyl chloride in the amidation step. This yields N-tert-butyl-2,6-dinitrobenzamide.

Reduction of the nitrobenzamide with hydrazine yields N-tert-butyl-2,6-diaminobenzamide.

Acetylation of the aminobenzamide yields N-tert-butyl-2,6-diacetamidobenzamide.

Example 18

Preparation of N-tert-butyl-3,4-diacetamidobenzamide

The method of Example 3 is repeated using 3,4-dinitrobenzoyl chloride in the amidation step. This yields N-tert-butyl-3,4-dinitrobenzamide.

Reduction of the nitrobenzamide with hydrazine yields N-tert-butyl-3,4-diaminobenzamide.

Acetylation of the aminobenzamide yields N-tert-butyl-3,4-diacetamidobenzamide.

Example 19

Preparation of N-tert-butyl-3,5-diacetamidobenzamide

The method of Example 3 is repeated using 3,5-dinitrobenzoyl chloride in the amidation step. This yields N-tert-butyl-3,5-dinitrobenzamide.

Reduction of the nitrobenzamide with hydrazine yields N-tert-butyl-3,5-diaminobenzamide.

Acetylation of the aminobenzamide yields N-tert-butyl-3,5-diacetamidobenzamide.

Preparation of Pharmaceutical Compositions

Example 20

The compound of Example 1 is admixed as a dry powder with a dry gelatin binder in an approximate 1:2 weight ratio. A minor amount of magnesium stearate is added as a lubricant. The mixture is formed into 240–270 mg tablets (80–90 mg of active benzamide) in a tablet press. If these tablets were administered to a patient suffering from a dopamine-associated neurodegenerative condition on a daily, twice daily or thrice daily regimen they would slow the progress of the patient's disease.

Example 21

The compound of Example 2 is admixed as a dry powder with a starch diluent in an approximate 1:1 weight ratio. The mixture is filled into 250 mg capsules (125 mg of active benzamide). If these capsules were administered to a patient suffering from a dopamine-associated neurodegenerative condition on a daily, twice daily or thrice daily regimen they would slow the progress of the patient's disease.

Example 22

The compound of Example 3 is suspended in a sweetened flavored aqueous medium to a concentration of approximately 50 mg/ml. If 5 mls of this liquid material was administered to a patient suffering from a dopamine-associated neurodegenerative condition on a daily, twice daily or thrice daily regimen they would slow the progress of the patient's disease.

Example 23

The compound of Example 4 is admixed as a dry powder with a dry gelatin binder in an approximate 1:2 weight ratio. A minor amount of magnesium stearate is added as a lubricant. The mixture is formed into 450–900 mg tablets (150–300 mg of active benzamide) in a tablet press. If these tablets were administered to a patient suffering from a dopamine-associated neurodegenerative condition on a daily, twice daily or thrice daily regimen they would slow the progress of the patient's disease.

Example 24

The compound of Example 14 is dissolved in a buffered sterile saline injectable aqueous medium to a concentration of approximately 5 mg/ml. If 50 mls of this liquid material was administered to a patient suffering from a dopamine-associated neurodegenerative condition such as Parkinson's disease on a daily, twice daily or thrice daily regimen this dose would slow the progress of the patient's disease.

It will be appreciated that any of the compounds of Formula II could be employed in any of these representative formulations, and that any of these formulations could be administered in any of these manners so as to treat any of the neurodegenerative conditions described in this specification.

Parkinson's Disease Screening Methods

Dopamine Depletion Studies.

C57BL/6J mice were pretreated with either vehicle (1% methyl cellulose) or a drag (p.o.) 30 min before MPTP. MPTP was dissolved in isotonic saline (0.9%) and given subcutaneously as a single dose of 15 mg free base/kg body weight to produce a reduction in striatal dopamine to about 0.5 nanomoles/mg protein. Groups of mice (n=8–10 per group) received either vehicle plus saline, vehicle plus MPTP, or drag plus MPTP. Seventy two hours after receiving MPTP, mice were sacrificed using cervical dislocation and the striata were excised. The tissue was homogenized in 0.4N perchioric acid, centrifuged, and the supernatant analyzed by high performance liquid chromatography/electrochemical detection (HPLC/ED) for dopamine levels. Supernatants were stored in a –90° C. freezer between the time of collection and analysis.

The drugs were combined with methyl cellulose and were homogenized in water for dosing. The dosage amount ranged from 10 to 50 mg/kg for CPI1160, CPI1189 and CPI1234, and from 50 to 100 mg/kg for CPI1020.

The results of representative experiments are provided in Tables 1 and 2. The results in Table 1 demonstrate that the compositions of this invention, as exemplified by CPI1160, CPI1189, and CPI1234 were effective in preventing dopamine depletion following MPTP challenge.

TABLE 1

Efficacy of CPI Compounds 1189, 1160, and 1234 at 30 mg/kg in the 15 mg/kg MPTP Model.

| COMPOUND | NANOMOLES DOPAMINE PER MG PROTEIN ± S.E.M. | % NON-MPTP CONTROL |
|---|---|---|
| methyl cellulose | 0.72 ± .05 | 54.1 |
| CPI1160 | 1.25 ± .05 | 93.9 |
| CPI1234 | 1.02 ± .05 | 76.7 |
| methyl cellulose | 0.56 ± .07 | 36.4 |
| CPI1189 | 1.37 ± .14 | 89.7 |

For comparison purposes the same tests were run on compositions based on CPI1020, a closely related benzamide compound. Results are shown in Table 2. At 50 mg/kg, CPI1189 offered complete protection from the neurotoxic action of MPTP (105% of control) while CPI1020 was not as effective (65% of control).

TABLE 2

Comparison of the Efficacies of CPI1189 and CPI1020 at 50 mg/kg in the 15 mg/kg MPTP Model.

| COMPOUND | NANOMOLES DOPAMINE PER MG PROTEIN ± S.E.M. |
|---|---|
| CPI1020 | 0.58 ± .14 |
| CPI1189 | 1.57 ± .11 |

What is claimed is:

1. A method for treating a patient suffering from a dopamine-associated neurodegenerative condition comprising administering to said patient an effective dopamine-associated neurodegenerative condition-treating amount of a pharmaceutical composition comprising a benzamide compound of the formula I:

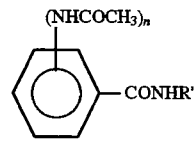

where R' is a saturated alkyl of from 3 to 5 carbon atoms and n is 1 or 2, in a pharmaceutically acceptable carrier.

2. The method of claim 1 wherein n is 1 and the acetamido group is at the 4 position of the ring.

3. The method of claim 1 wherein n is 1 and the acetamido group is at the 2 position of the ring.

4. The method of claim 1 wherein n is 1 and the acetamido group is at the 3 position of the ring.

5. The method of claim 1 wherein R' is tert-butyl.

6. The method of claim 1 wherein the benzamide compound is N-tert-butyl-4-acetamidobenzamide.

7. The method of claim 6 wherein the carrier is an oral carrier, the administering is orally administering and the effective dopamine-associated neurodegenerative condition-treating amount is one to five oral doses per day each providing from 1 to 10 mg/kg of N-tert-butyl-4-acetamidobenzamide to the patient.

8. The method of claim 6 wherein the carrier is an injectable carrier, the administering is by injection and the effective dopamine-associated neurodegenerative condition-treating amount is 0.1 to 10 mg/kg/day of N-tert-butyl-4-acetamidobenzamide.

9. A method for treating a patient suffering from a dopamine-associated progressive loss of central nervous system function comprising administering to said patient an effective dopamine-associated progressive central nervous system function loss-treating amount of a pharmaceutical composition comprising a benzamide compound of the formula I:

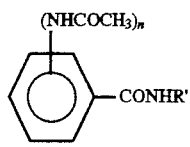

where R' is a saturated alkyl of from 3 to 5 carbon atoms and n is 1 or 2, in a pharmaceutically acceptable carrier.

10. The method of claim 9 wherein n is 1 and the acetamido group is at the 4 position of the ring.

11. The method of claim 9 wherein n is 1 and the acetamido group is at the 2 position of the ring.

12. The method of claim 9 wherein n is 1 and the acetamido group is at the 3 position of the ring.

13. The method of claim 9 wherein R' is tert-butyl.

14. The method of claim 9 wherein the benzamide compound is N-tert-butyl-4-acetamidobenzamide.

15. The method of claim 14 wherein the carrier is an oral carrier, the administering is orally administering and the effective dopamine-associated progressive loss of central nervous system function-treating amount is one to five oral doses per day each providing from 1 to 10 mg/kg of N-tert-butyl-4-acetamidobenzamide to the patient.

16. The method of claim 15 wherein the dopamine-associated progressive loss of central nervous system function is Parkinson's disease.

17. The method of claim 14 wherein the carrier is an injectable carrier, the administering is by injection and the effective dopamine-associated progressive loss of central nervous system function-treating amount is 0.1 to 10 mg/kg/day of N-tert-butyl-4-acetamidobenzamide.

18. The method of claim 17 wherein the dopamine-associated progressive loss of central nervous system function is Parkinson's disease.

19. A method for treating a patient suffering from a condition characterized by progressive loss of central nervous system function due to mitochondrial dysfunction comprising administering to said patient an effective progressive central nervous system function loss due to mitochondrial dysfunction-treating amount of a pharmaceutical composition comprising a benzamide compound of the formula I:

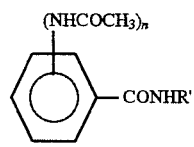

where R' is a saturated alkyl of from 3 to 5 carbon atoms and n is 1 or 2, in a pharmaceutically acceptable carrier.

20. The method of claim 19 wherein n is 1 and the acetamido group is at the 4 position of the ring.

21. The method of claim 19 wherein n is 1 and the acetamido group is at the 2 position of the ring.

22. The method of claim 19 wherein n is 1 and the acetamido group is at the 3 position of the ring.

23. The method of claim 19 wherein R' is tert-butyl.

24. The method of claim 19 wherein the benzamide compound is N-tert-butyl-4-acetamidobenzamide.

25. The method of claim 24 wherein the carrier is an oral carrier, the administering is orally administering and the effective progressive central nervous system function loss due to mitochondrial dysfunction—treating amount is one to five oral doses per day each providing from 1 to 10 mg/kg of N-tert-butyl-4-acetamidobenzamide to the patient.

26. The method of claim 24 wherein the carrier is an injectable carrier, the administering is by injection and the effective progressive central nervous system function loss due to mitochondrial dysfunction—treating amount is 0.1 to 10 mg/kg/day of N-tert-butyl-4-acetamidobenzamide.

* * * * *